United States Patent
Wu et al.

(10) Patent No.: US 7,893,616 B2
(45) Date of Patent: Feb. 22, 2011

(54) PROCESS TO DETERMINE ENZYME ACTIVITY

(75) Inventors: Haifeng M. Wu, Columbus, OH (US); Ming Jin, Columbus, OH (US); Michael G. Bissell, Reynoldsburg, OH (US); Spero R. Cataland, Westerville, OH (US)

(73) Assignee: Ohio State University, Columbus, OH (US)

( * ) Notice: Subject to any disclaimer, the term of this patent is extended or adjusted under 35 U.S.C. 154(b) by 301 days.

(21) Appl. No.: 11/711,946

(22) Filed: Feb. 27, 2007

(65) Prior Publication Data

US 2008/0206787 A1 Aug. 28, 2008

Related U.S. Application Data

(60) Provisional application No. 60/777,093, filed on Feb. 27, 2006.

(51) Int. Cl.
*H01J 17/26* (2006.01)

(52) U.S. Cl. ..................................... 313/564

(58) Field of Classification Search ........................ None
See application file for complete search history.

(56) References Cited

U.S. PATENT DOCUMENTS

| 6,926,894 B2 | 8/2005 | Laemmle et al. |
| 7,163,686 B1 | 1/2007 | Silverman |

OTHER PUBLICATIONS

ADAMTS 13 Activity Assay 1 pg., 2007.

Wu, Haifeng, et al., Application of SELDI-TOF Mass Spectrometry in Clinical Evaluation of Thrombotic Thrombocytopenic Purpura. pp. 1-19.
Determination of ADAMTS13 Anitbody Activity. pp. 1-2.
Protocol for Using Low Curve to Determine ADAMTS13 Activity. pp. 1-3.
Cataland, S.R., Full Evaluation of an Acquired Case of Thrombotic Thrombocytopenic Purpura Following the Surgical Resection of Glioblastoma Multiforme. pp. 2733-2737.
ADAMTS13 Activity Assay (Low Curve). Feb. 15, 2007, pp. 1-2.
Jin, M., et al. A Rapid Test for the Diagnosis of Thrombotic Thrombocytopenic Purpura Using Surface Enhanced Laser Desorption/Ionization Time-of-Fligh (SELDI-TOF)-Mass Spectrometry. Journal of Thrombosis and Haemostasis, 4: 333-338, 2005, International Society on Thrombosis and Haemostasis.
Cataland, S.R., An Evaluation of Cyclosporine Alone for the Treatment of Early Recurrences of Thombotic Thrombocytopenic Purpura. pp. 1162-1164, 2006, International Society on Thrombosis and Haemostasis.

*Primary Examiner*—Karen Cochrane Carlson
*Assistant Examiner*—Bin Shen
(74) *Attorney, Agent, or Firm*—Stephen A. Bent; Foley & Lardner LLP

(57) ABSTRACT

The present invention provides for various processes for determining enzyme activity. In one embodiment, a process for detecting an enzyme activity includes contacting a blood component with a substrate comprising a cleavage site of the enzyme and a tag moiety to produce a sample comprising a cleavage product having a known mass, and placing the sample in contact with a SELDI sample chip which has surface moieties which bind to the cleavage product. In another embodiment, the process further includes subjecting the SELDI sample chip to SELDI mass spectrometry to identify the cleavage product. The present invention also provides for a kit which includes a SELDI sample chip having surface moieties capable of binding to an enzyme cleavage product.

36 Claims, 7 Drawing Sheets

PROCESS TO DETERMINE ENZYME ACTIVITY

The present application claims the benefit of priority to U.S. provisional application No. 60/777,093, filed Feb. 27, 2006, the entire contents of which are incorporated herein by reference.

FIELD OF THE INVENTION

The present invention relates to the field of medicine and diagnosis and clinical evaluation of blood clotting disorders. More specifically the present invention relates to a process that provides for rapid and sensitive analysis of enzyme activity and antibody activity in a biological sample.

BACKGROUND

Abnormal thrombotic events can give rise to heart attacks, stroke and deep vein thrombosis. One clotting disorder, Thrombotic Thrombocytopenic Purpura (TTP), is a thrombotic microangiopathy characterized by hemolytic anemia, consumptive thrombocytopenia, and ischemic injury. The pathogenesis of TTP is attributed to the presence of an Unusually Large von Willebrand Factor (ulvWF) multimers that lead to platelet clumping and subsequent thrombosis. vWF is primarily synthesized by vascular endothelial cells and secreted as a polymer with a $M_r$ of greater than 500,000 kDa. These ultra-large multimers are highly active to promote platelet thrombi. Under normal physiological conditions, a metalloprotease enzyme, ADAMTS-13, cleaves vWF multimers into smaller protein units ranging from 500 to 20,000 kDa. Impairment of ADAMPTS-13 activity, caused either by hereditary deficiency or by acquired autoantibodies that specifically inhibit ADAMTS-13 function, leads to excessive accumulation of ulvWF and the eventual onset of TTP. The majority of clinically observed TTP cases in adults are acquired, with patients showing detectable levels of autoantibodies to ADAMTS-13.

Clinical management of TTP requires a rapid diagnosis followed with a prompt treatment. Plasma exchange therapy has been demonstrated to be the most successful therapy. It effectively replaces ADAMTS-13 and/or removes the ADAMTS-13 inhibitor in the case of acquired TTP. Without the prompt diagnosis and initiation of therapy, mortality for TTP is greater than 80%. However, timely treatment with plasma exchange greatly improves clinical outcome by inducing a remission in greater than 80% of patients. Therefore, a clinical test that can rapidly detect severe deficiencies of ADAMTS-13 activity associated with acute TTP is in great demand.

Since the discovery of ADAMTS-13 deficiency as a causal factor in TTP's pathogenesis, many attempts were made to measure plasma ADAMTS-13 activity in the patients with TTP. Furlan and Tsai independently reported original vWF protease assays. In both of their assays, human vWF, purified from plasma, was used as a substrate of ADAMTS-13 protease under a denatured condition using either urea or guanidine-HCl. After incubation with the tested plasma sample, ADAMPTS-13 activities were estimated using electrophoresis/Western blot that detect either vWF substrate disappearance or generation of vWF cleavage products. The assays are tedious, technically challenging, and difficult to standardize. Other diagnostic tests have also been reported since the original works by Furlan and Tsai. They include collagen binding assays, immunoradiometric assay and ristocetin cofactor activity assays. Although these assay methods require less time to complete, they do not directly measure the vWF cleavage by ADAMTS-13 protease.

Recently, a recombinant vWF protein containing a GST fusion protein and a Histidine tag (vWF73) was developed. This substrate contains a specific cleavage site for ADAMTS-13 (Tyr1605-Met1606) and has been used to measure ADAMTS-13' activity in TTP patients. The assay demonstrated excellent reproducibility but the test turnaround time is at least 24 hours because it utilizes a Western blot to detect the cleavage product.

Therefore there is a need for a rapid, easy to perform, and functionally relevant ADAMTS-13 assay to provide clinical data for diagnosis and effective management of patients suspected to have TTP.

SUMMARY

The present invention is useful in determining the presence of blood clotting disorders which give rise to heart attack, stroke, deep vein thrombosis, and arterial thrombotic disorders. For example, under normal physiological conditions, a metalloprotease enzyme, ADAMTS-13, cleaves vWF multimers into smaller protein units ranging from 500 to 20,000 kDa. However, impairment of ADAMPTS-13 activity leads to excessive accumulation of ulvWF and the eventual onset of blood clotting disorders.

In one embodiment of the present invention, a process for detecting an enzyme activity includes contacting a blood component with a substrate comprising a cleavage site of the enzyme and a tag moiety to produce a sample comprising a cleavage product having a known mass, and placing the sample in contact with a SELDI sample chip which has surface moieties which bind to the cleavage product. The process can further include washing the SELDI sample chip to remove blood product components that do not selectively bind to the surface moieties of the SELDI sample chip, and then subjecting the SELDI sample chip to SELDI mass spectrometry to identify the cleavage product.

In another embodiment, the process for detecting ADAMTS-13 activity includes providing blood component; providing a substrate comprising an enzyme cleavage site and a tag moiety; contacting the blood component with the substrate, thereby forming a sample which includes a cleavage product having a known mass, and placing the sample in contact with a SELDI sample chip comprising surface moieties which bind to the cleavage product.

In yet another embodiment of the present invention, the process for detecting ADAMTS-13 activity includes providing a blood component; contacting a blood component with a substrate that includes an ADAMTS-13 cleavage site and a tag moiety to initiate a cleavage reaction and to produce a sample comprising a cleavage product having a known mass; terminating the reaction; adding an internal control to the sample; removing blood product components that do not selectively bind to the surface moieties of the SELDI sample chip; and placing the sample comprising the cleavage product in contact with a SELDI sample chip where the sample chip has surface moieties which bind to the cleavage product and the internal control.

DESCRIPTION OF THE FIGURES

The various embodiments of the present invention can be understood with reference to the following figures.

DETAILED DESCRIPTION

Figure 1:
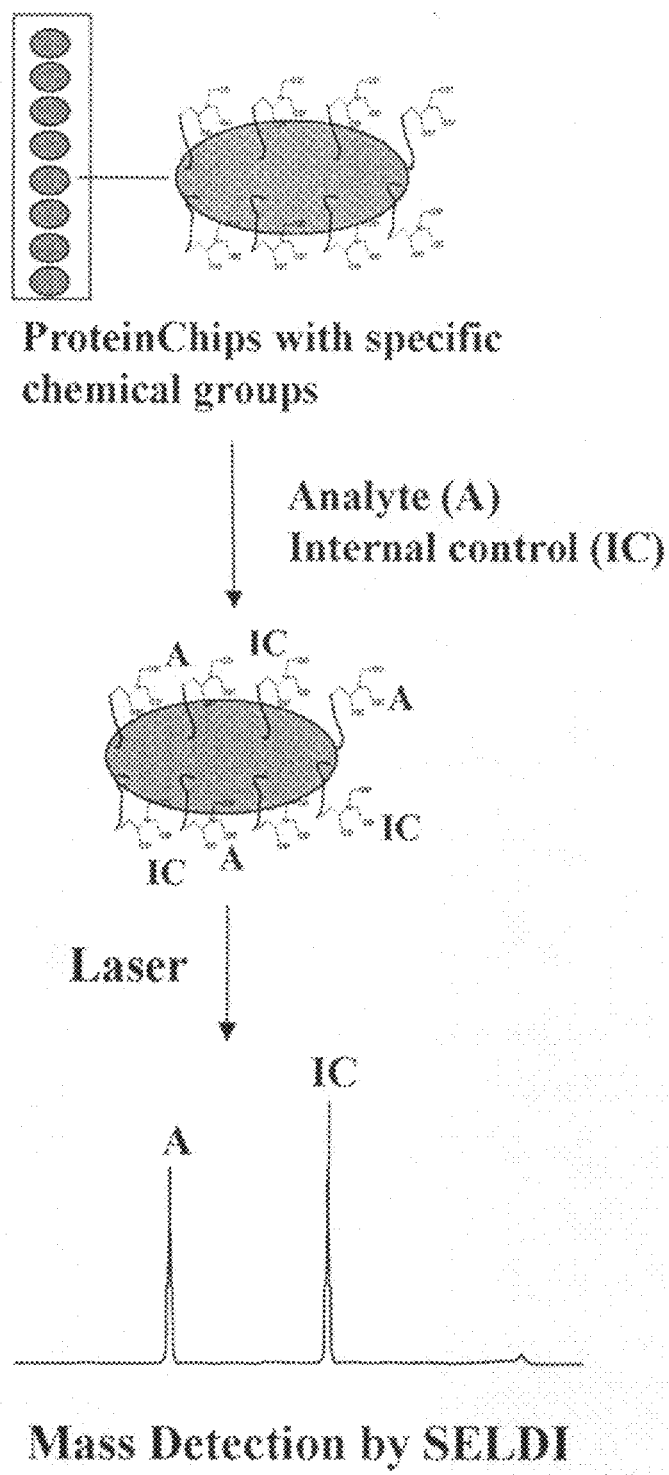
FIG. 1 illustrates the use of internal control (IC) in SELDI-TOF based test, according to an embodiment of the invention.

The present invention relates to a method in which the activity of enzymes can be detected to diagnose blood clotting disorders. The methods provided according to the various embodiments of the present invention produce a rapid diagnostic test to help clinicians diagnose an illness and to initiate the proper therapy. The methods also provide a biomarker which predicts the recurrence of blood disorders and allows for early prophylactic treatment to improve clinical outcome.

In one embodiment of the present invention, a process for detecting an enzyme activity includes contacting a blood component with a substrate comprising a cleavage site of the enzyme and a tag moiety to produce a sample comprising a cleavage product having a known mass, and placing the sample in contact with a SELDI sample chip which has surface moieties which bind to the cleavage product. The process can further include washing the SELDI sample chip to remove blood product components that do not selectively bind to the surface moieties of the SELDI sample chip, and then subjecting the SELDI sample chip to SELDI mass spectrometry to identify the cleavage product.

The process can detects enzymes that have activity to produce a peptide containing a histidine tag. The process can also determine the amount of activity an enzyme having activity to produce a peptide comprising a tag moiety which binds to a metal charged on an IMAC protein Chip.

In another embodiment, the process for detecting ADAMTS-13 activity includes providing a blood component; providing a substrate comprising an ADAMTS-13 cleavage site and a tag moiety; contacting the blood component with the substrate, thereby forming a sample which includes a cleavage product having a known mass, and placing the sample in contact with a SELDI sample chip having surface moieties which bind to the cleavage product. For example, the method can determine the ADAMTS-13 activity for the diagnosis of TPP, assess the patient's response to therapy for TTP, and also predict recurrences of TTP.

The substrate includes a recombinant protein that produces a cleaved product, the cleaved product by ADAMTS13 is detected as a peak by SELDI mass spectrometer. However, the recombinant vWF protein (substrate) can be modified or engineered differently that give rise to a product of different molecular weight upon cleavage by ADAMTS13.

A tag moiety includes any tag moiety that can bind to a SELDI protein chip and subsequently quantified specifically. Examples of tag moieties include, but are not limited to, maltose binding protein tag, glutathione-S-transferase (GST) tag, biotin tag, avidin tag, and histidine tag.

In another embodiment, the process can further include washing the SELDI sample chip to remove blood product components that do not selectively bind to the surface moieties of the SELDI sample chip, and then subjecting the SELDI sample chip to SELDI mass spectrometry to identify the cleavage product. In the examples below, the SELDI sample chip was washed in 50 mM sodium phosphate, pH 7.2, 0.8 M sodium chloride, with 0.1% Triton X-100. In general, a buffer of high stregency, such as containing high concentration of salt and detergent, that wash off components that do not bind to protein Chip, for example, the IMAC chip in this application. In turn, only cleaved product and IC will stay bound to the chip and then detected by mass spectrometer.

Surface Enhanced Laser Desorption/Ionization Time Of Flight Mass Spectrometry (SELDI-TOF-MS) provides ability of rapid protein/peptide detection and quantification. One distinguishable feature of SELDI-TOF-MS involves the surface chemistry of proteinchips that allows for selective purification of protein/peptide candidates prior to analysis by mass spectrometry.

It has been found that SELDI-TOF does provide adequate sensitivity for separation and measurement of peptides and proteins in biological samples. A feature of SELDI-TOF comes from different arrays or chip surfaces that are available for isolating a specific compound or a subset of substances. These arrays allow for selective purification and/or enrichment of target peptides/proteins of interest on the array. Following ionization by a laser beam, the target analyte(s) can be measured by the mass spectrometer.

Several kinds of arrays are available, each coated with specific chemical grops such as immobilized metal affinity captur (IMAC) array, cation or anion exchange array, or an array with a hydrophobic property. Therefore, it is possible to pre-select a particular array based on the properties of the target analytes, enrich a target molecule, an then detect it by mass spectrometer.

ProteinChip arrays are used to selectively bind whole classes of molecules in crude samples for detection by the ProteinChip reader such as SELDI-TOF-MS. Each chip array contains chemically treated surfaces (cationic, anionic, hydrophobic, hydrophilic, metal binding etc.) or biochemically treated surfaces (bound antibody, receptor, DNA, etc.) for specific interaction with molecules of interest. Specific examples of protein Chips include chips that allow for antibody antigen reaction, receptor-ligand binding, and DNA-binding protein applications.

SELDI sample chip is charged with a compound comprising a metal which include, but are not limited to, nickel, iron II, iron III, calcium, magnesium, manganese, copper, zinc and mixtures thereof.

The SELDI sample chip can be a IMAC ProteinChip charged with nickel sulfate.

The readout from the mass spectrometer is relatively easy to interrupt. The mass to charge ratio (m/z), also described as the peak position, provides the identity of the analyte. The relative abundance of the analyte can be determined by evaluating the intensity of the peak or peak area. However, the mass spectrometry is not inherently quantitative. When peptides or proteins are ionized, the extent of ionization varies from sample to sample, causing significant inter-assay variation. With regard to SELDI-TOF, there are possible heterogeneities in surface chemistry between different array spots or between different batches of protein arrays.

Therefore, in another embodiment of the present invention the method includes inclusion of an internal control for calibration when SELDI-TOF is used for quantification of a compound. The internal control is a known compound that interacts specifically with the selected array as the analyte. When the same amount of internal control is added to all the measurements, the quantity of the analyte can be calculated as a ratio to the internal control. This approach minimizes the variations due to chemical matrix of the arrays or due to the detection variations intrinsic to mass spectrometry.

In another embodiment of the present invention, the process for detecting ADAMTS-13 activity includes providing a blood component; contacting a blood component with a substrate that includes an ADAMTS-13 cleavage site and a tag moiety to initiate a cleavage reaction and to produce a sample comprising a cleavage product having a known mass; terminating the reaction; adding an internal control to the sample; removing blood product components that do not selectively bind to the surface moieties of the SELDI sample chip; and placing the sample comprising the cleavage product in contact with a SELDI sample chip where the sample chip has surface moieties which bind to the cleavage product and the internal control.

FIG. 1 illustrates the use of internal control (IC) in SELDI-TOF based test. It illustrates the readout with an IC. As illustrated, the analyte is quantified as a ratio to IC, in order to minimize inter-assay variations caused by experiments, proteinChips, and mass spectrometer.

PNP represents pooled normal plasma. It is the standard for lots of clinical assays. For example, amount of ADAMTS13 activity in pnp is considered to be 100%. A standard can be made from either purified ADAMTS13 or engineered ADAMTS13. Indeed, a test can be designed in variety ways and volumes as long as appropriate ratio of subtrate (vWF73) to enzyme (ADAMTS13) is maintained that give rise to the amount of product (cleaved product of 7721 dalton).

Example 1 described below shows that when a vWF fusion protein with histidine tag was used as a substrate for ADAMTS13, a 7739 dalton peptide containing a 6× histidine tag was generated in an amount corresponding to the plasma ADAMTS13 activity in TTP patients. This finding creates the preconditions for the design of an assay in which ADAMTS13 cleaved product is selected by IMAC proteinChip and then measured by SELDI-TOF mass spectrometer.

There are a number of metal binding proteins in plasma that bind to the IMAC proteinChip under stringent washing conditions. Thus, the capture of 7739 dalton peptide by IMAC proteinChip is realively specific in a way analogous to the antibody/antigen reaction in the immuno-based assays. Moreover, the mass of the analyte, a 7739 dalton peptide derived from the cleavage of vWF by ADAMTS13, is in the best mass range whereby a compound undergoes adequate ionization by laser beam and then can be effectively detected by the SELDI-TOF mass spectrometer.

SELDI-TOF appears to offer the good test sensitivity and reproducibility when analyzing peptides with a mass range from about 1 kD to about 50 kD, and in another example from about 5 kD to about 20 kD.

In adult patients, TTP is mostly due to the production of ADAMTS13 autoantibodies, which impair ADAMTS13 function leading to an acquired ADAMTS13 deficiency. In the absence of ADAMTS13, vWF undergoes excessive polymerization that eventually leads to an uncontrolled platelet thrombosis and onset of TTP. With a timely diagnosis, TTP patients usually respond well to daily plasma exchange therapy. However, more than half of these patients experience disease recurrences, resulting in considerable mortality and morbidity.

Because the treatment with plasma exchanges (PE) can reduce the mortality of TTP from greater than 80% to less than 20%, a rapid diagnostic test is critical for clinicians to initiate timely therapy. In contrast, many patients with other serious medical problems such as complications of bone marrow transplantation, human immunodeficiency virus infection, or disseminated malignancy may present similar clinical manifestations as TTP. Most of these patients however have normal ADAMTS13 function and do not typically respond to PE therapy. An adequate measurement of ADAMTS13 activity will help clinicians correctly recognize these complicated clinical conditions, prevent wasting of valuable blood components, and avoid unnecessary complications related to PE therapy and catheter placement. Since the implementation of our SELDI-TOF based method, fast turnaround time for the detection of ADAMTS13 activity has greatly helped us in making the correct diagnosis, instituting appropriate therapy, and improving patient outcomes.

Likewise, several other methodologies to detect ADAMTS13 activity have been reported. The current regimen of PE therapy has generally been effective in the induction of clinical remission. However, more than half of TTP patients still experience disease recurrences, resulting in considerable mortality and morbidity. The post-thrombotic sequelae in TTP include chronic renal insufficiency and neurological complications. Clinical biomarkers that predict disease activity and TTP's recurrences would be of tremendous value, and allow for early prophylactic treatment. In our initial study, we correlated TTP disease activity with ADAMTS13 antibody level in sequentially collected samples from three TTP patients. Interestingly, one of the three patients displays clear disconcordance between antibody amount and clinical course. This discovery prompted us to use our SELDI-TOF mass spectrometer based method to evaluate the inhibitory titer of ADAMTS13 autoantibody in all samples from this patient. Consistent with our prediction, ADAMTS13 antibody functional activity indeed correlated with the clinical course of the disease. This initial discovery suggests that the functional characteristics or neutralizing activity of the antibody inhibitor may be of value as a surrogate biomarker to evaluate disease activity in TTP and to predict TTP recurrences.

The application of SELDI-TOF mass spectrometry to measure ADAMTS13 activity and to evaluate ADAMTS13 autoantibody activity are both useful paramerters in the pathobiology and clinical manifestation of TTP.

In another embodiment, the present invention provides for a kit that includes a SELDI sample chip having surface moieties capable of binding to an enzyme cleavage product. In another embodiment the enzyme kit includes a substrate of ADAMTS-13 and the cleavage product is an ADAMST-13 cleavage product.

EXAMPLES

The following examples are included to provide additional guidance to those skilled in the art of practicing the claimed invention. These examples are provided as representative of the work and contribute to the teaching of the present invention. Accordingly, these examples are not intended to limit the scope of the present invention in any way.

Example 1

Measurement of ADAMTS13 Activity

The cleavage reaction, containing 2.2 µL of plasma and 1.8 µg VWF73 in a 30 µL of buffer (5 mM Tris HCl, 5 mM NaCl 1 mM $BaCl_2$, pH 7.5), was performed for 60 min at 37° C. and terminated by boiling at 95° C. for 2 min. Each experiment included a standard curve performed under identical conditions except that the plasma sample ws replaced by pooled normal plasma (PNP) dilutes at 50%, 25%, 10%, 5%, 2.5% in 100 mM NaCl containing 0.1% bovine serum albumin (BSA).

This experiment was performed using a SELDI-TOF Bioprocessor. Each spot on the IMAC ProteinChip was charged with 50 mM nickel sulfate for 15 min. The spot was then wshed extensively with washing buffer (50 mM sodium phosphate, pH 7.2). Twenty µL of VWF73 cleaveage product (described above) and 40 µL of internal standard were mixed and added to each spot for 30 min incubation at room temperature with constant shaking. Afterwards, each spot was washed five times with 200 µL of washing buffer with three washes for 5 min. and then two quick washes. This was followed by one quick wash with 1 mM 4-(2-hydroxyethyl)-1-poperazineethanesulfonic acid (HEPES), pH 7.0. Finally, 1 µL of energy absorbing molecule (EAM) solution (100% saturated Sinapinic acid in 50% acetonitrile and 0.5% trifluoroacetic acid) was added to each spot, the chips were allowed to air dry, and then the step was repeated. IMAC ProteinChips were analyzed by SEDLI-TOF-MS instrument (Proetein Biology System II, Ciphergen, Fremont, Calif., USA). The data collection was acquired using the following settings with optimized range of mass to charge ratio (m/z) from 3000 to 20 000; laser intensity at 165; detector sensitivity at 8. After baseline subtraction, data was analyzed with ProteinChip Software (version3.1). Peak labeling was performed manually for cleaved peptide and internal control based on calculated molecular weight. The peak area was used to quantify the analytes. Because of the fact that virtually all anayltes displayed a signal to noise ratio >10 we defined the peak areas by slope-based option using the peak boundary: 25 times the noise per 11 times expected peak width. Data was then exported to Excel for further analysis.

To inactivate ADAMT-13 protease activity, patient's plasma was heated for 30 minutes at 56° C. followed by centrifugation for 15 minutes at 15,000 g to remove insoluble proteins. Twenty microliters of supernatant were mixed with 20 uL of PNP and incubated at 37° C. for 1 hour. An aliquot of the mix was then assayed for residual ADAMTS-13 activity, as described above. Inhibition was indicated by a decrease in the amount of cleaved peptide by PNP after incubation with patient's plasma. Results were expressed as percentage of PNP ADAMTS-13 activity neutralized by and equal amount of patient's plasma.

Figure 2:
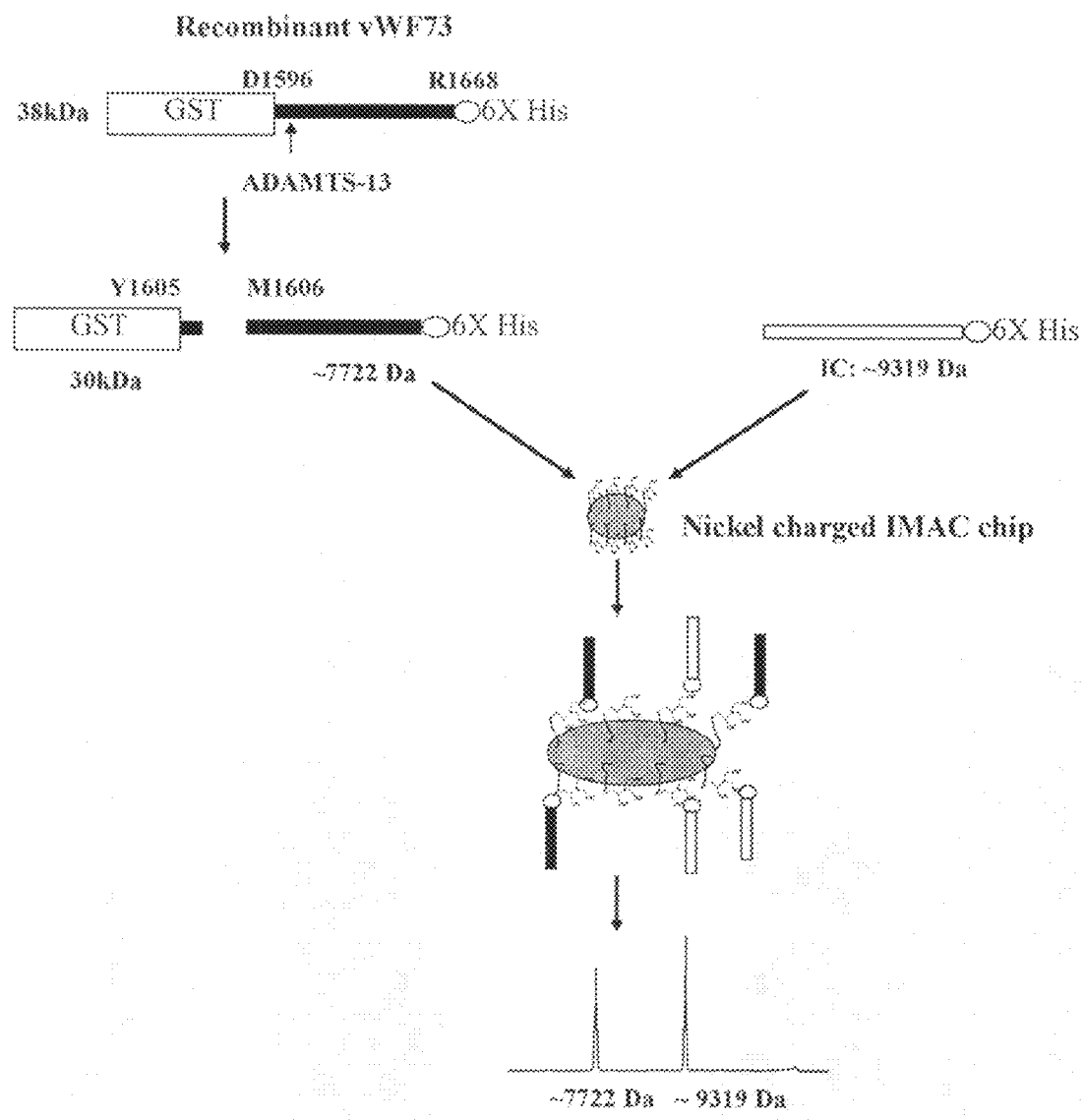
FIG. 2 illustrates a recombinant vWF73 fusion protein containing the ADAMTS13 cleavage site is cleaved by ADAMTS13, generating a ~7722 Dalton peptide tagged with Histidine, according to an embodiment of the invention.

FIG. 2 illustrates the principle of how ADAMTS13 activity is measured. Recombinant vWF73 fusion protein containing the ADAMTS13 cleavage site is cleaved by ADAMTS13, generating a ~7722 Dalton peptide tagged with Histidine. This small peptide specifically binds to Nickel charged IMAC proteinChip and then is quantified by SELDI-TOF with a proper internal control.

Figure 3:
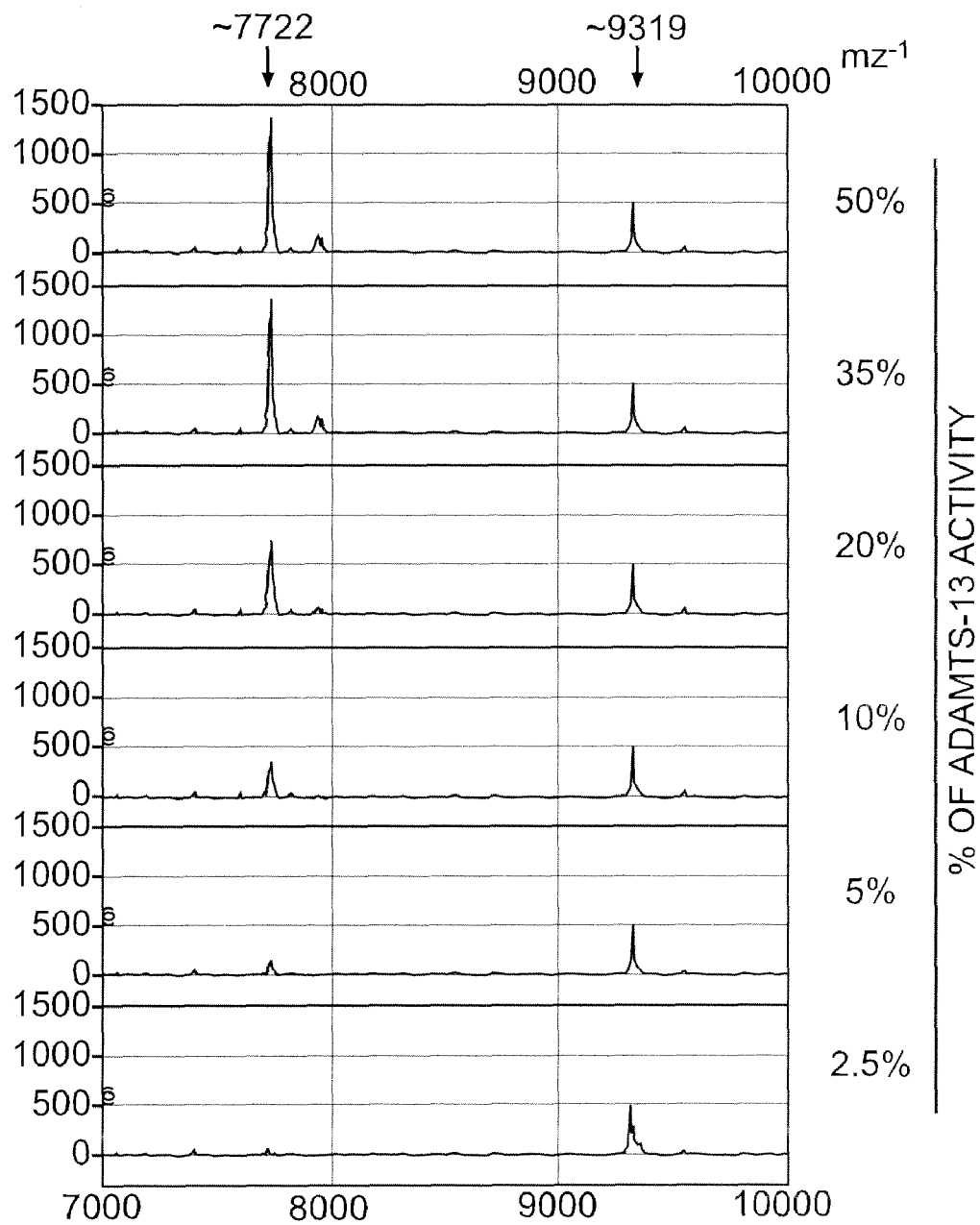
FIG. 3 is a graph illustrating the quantification of VWF73 cleavage by ADAMTS-13 using SELDI-TOF mass spectrometry and the amount of cleaved product 7722 Da peptide, when different percentages of PNP containing ADAMST-13 were incubated with a fixed amount of recombinant VWF for 60 minutes at 37° C., according to an embodiment of the present invention.

FIG. 3 shows quantification of vWF73 cleavage by ADAMTS13 using SELDI-TOF mass spectrometry. The samples containing different amount of ADAMTS13 were incubated with a fixed amount of recombinant vWF for 60 minutes at 37° C. The cleaved product, 7722 dalton peptide, was then detected by SELDI-TOF. An internal standard (9319 dalton peptide) was added before ionization reaction and SELDI TOF analysis.

Figure 4:
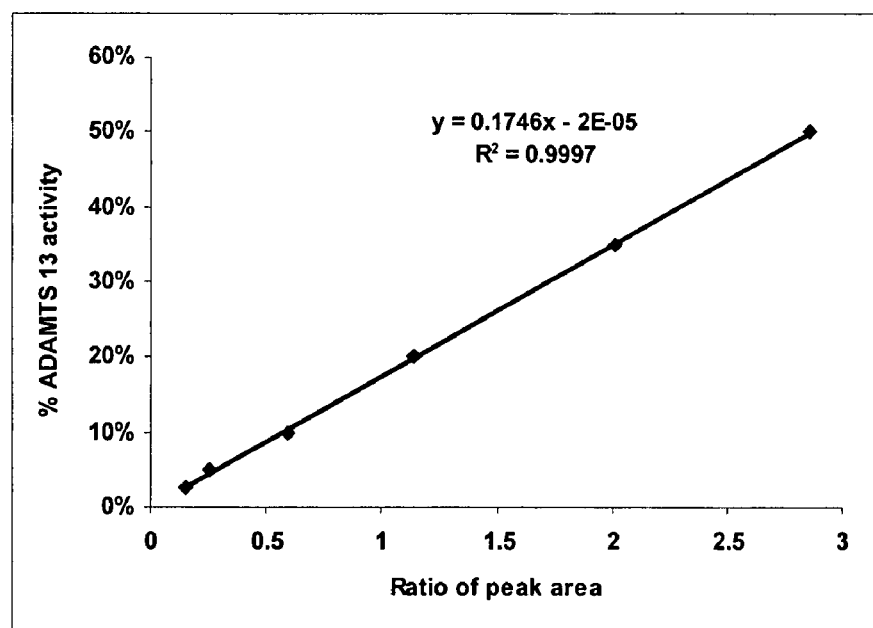
FIG. 4 shows a dose-dependent cleavage of vWF73 by ADAMTS13. Assays were performed using a fixed amount of vWF73 and various amounts of ADAMTS13, according to an embodiment of the invention.

FIG. 4 shows a dose-dependent cleavage of vWF73 by ADAMTS13. Assays were performed using a fixed amount of vWF73 and various amounts of ADAMTS13. vWF cleavage product, 7722 dalton peptide, was quantified by SELDI TOF. The standard curves were plotted using peak ratios (ratio of 7722/9319) as a function of ADAMTS13 in the reaction.

The method described above in Example 1 detected ADAMTS-13 activity at as low as 2.5% in patient plasma. The test reproducibility was excellent in the ranges when ADAMTS-13 activity was >10%, however, coefficiency of variation increased up to about 50% when ADAMTS-13 activity in the lower range.

Example 2

Modified Method to Detect ADAMTS13 Activity in the Lower Range

In order to improve both test detection sensitivity and test reproducibility when the ADAMTS13 activity in the sample is low, the above procedure was modified to allow for a longer incubation time (14-18 hours) of patient plasma with recombinant vWF substrate (vWF73). This condition greatly maximized the amount of product (7,722 daltons) generated from vWF73 by ADAMTS-13. This in turn improved the detection sensitivity of ADAMTS-13 to as low as 0.31% of ADAMTS-13 activity. At the same time, the modified test greatly enhanced the test reproducibility when ADAMTS-13 activity in the sample is low. Three control samples were repeated using these modified methods five times, and the inter-assay variation give a CV of less than 20%. Furthermore, because many TTP patients demonstrate less than 5% ADAMTS-13 activity through out the courses of treatment and clinical remission, a better detection sensitivity may allow us to determine the hemostatic level of ADAMTS-13 activity required to prevent clinical manifestation of TTP. Additionally, this modified method may enable the stratification of the TTP patient with respect to responses to therapy and risks of disease relapses during clinical remission.

Figure 5:
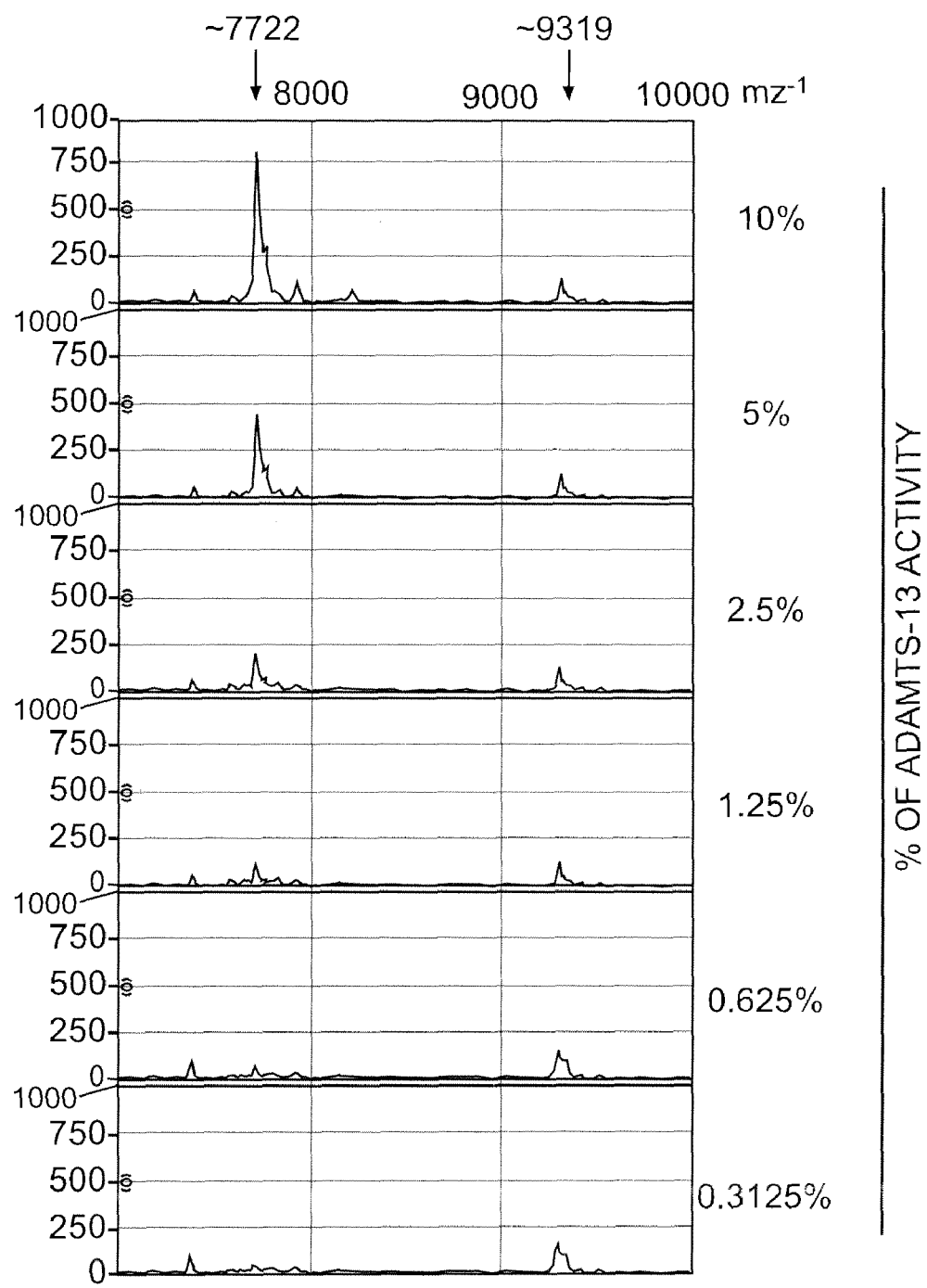
FIG. 5 shows low Curve quantification of ADAMTS13 activity by SELDI-TOF mass spectrometry, according to an embodiment of the present invention.

FIG. 5 shows low Curve quantification of ADAMTS13 activity by SELDI-TOF mass spectrometry. The standards containing different percentages of ADAMTS13 (0.31 to 10%) were incubated with a fixed amount of recombinant VWF 73 for 14-18 hours at 37° C. The cleaved product, 7,722 Dalton peptide, was then measured by SELDI-TOF. An internal standard (9319 Dalton peptide) was added to each reaction before ionization reaction during SELDI TOF analysis.

Figure 6:
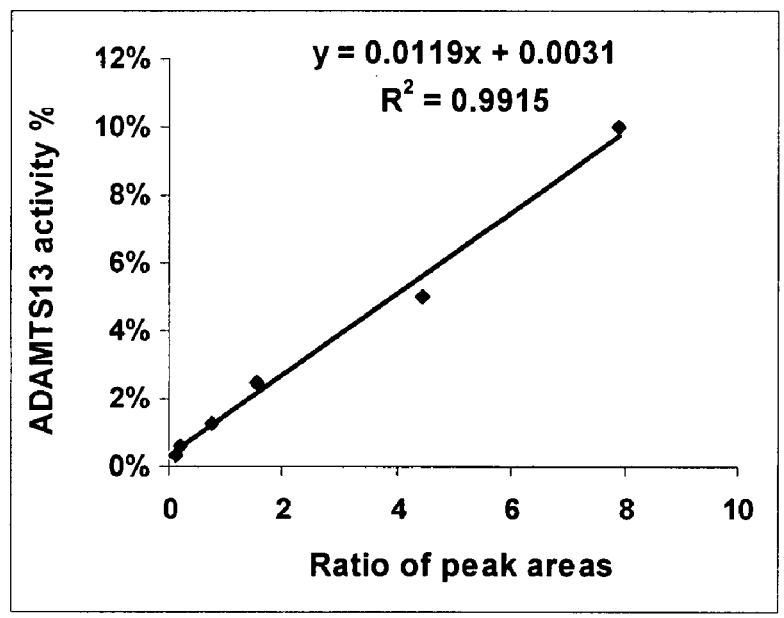
FIG. 6 shows a representative standard low curve. Incubations were performed for 16 hours at 37° C. using a fixed amount of recombinant VWF73; according to an embodiment of the invention.

FIG. 6 shows a representative standard low curve. Incubations were performed for 16 hours at 37° C. using a fixed amount of recombinant VWF73. The low curve contains standards with ADAMTS13 activity from 0.31% to 10%. vWF cleavage product, 7722 Dalton peptide, was quantified as a peak ratio, peak area of 7,722 Dalton peptide divided by respective peak area of internal control.

Example 3

Clinical Validation of Method for Measurement of ADAMTS13

Figure 7:
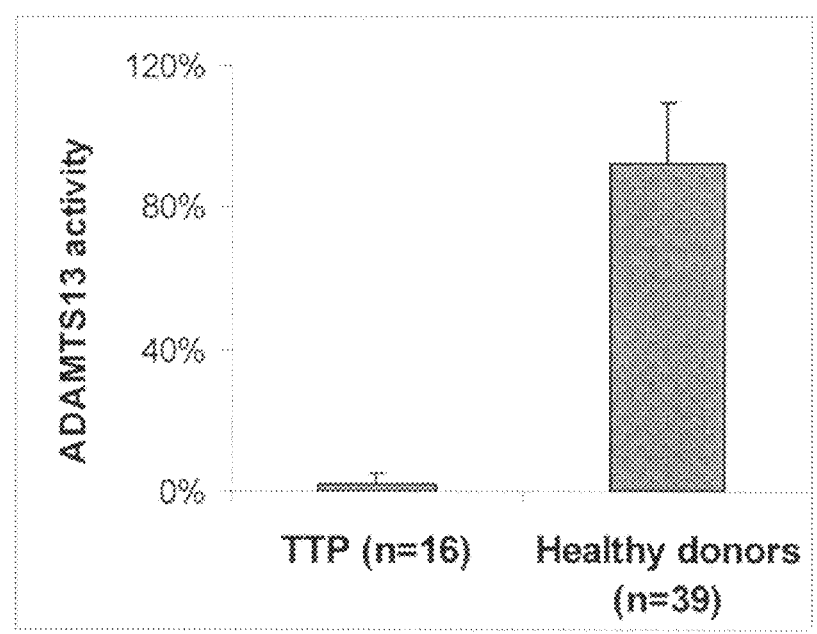
FIG. 7 shows clinical validation of ADAMTS13 activity in normal donors and in the patients with diagnosis of idiopathic TTP, according to an embodiment of the invention.

FIG. 7 shows Clinical validation of ADAMTS13 activity in normal donors and in the patients with diagnosis of idiopathic TTP. 39 healthy donors and 16 patients with diagnosis of idiopathic TTP were selected for clinical validation. Clinical characteristics and laboratory values of 16 TTP patients are shown in Table 1. All samples were collected at the time of clinical presentation of TTP and prior to start of plasma exchange therapy. All healthy doners exhibited normal levels of ADAMTS-13 activity while values obtained from patients were of <5%. This demonstrated the test results from this method accurately differentiate TTP patients from subjects without disease.

Example 4

Determination of ADAMTS13 Activity using this Method

Most cases of TTP are due to production of ADAMTS13 autoantibody that somehow impairs the functional properties of ADAMTS13 in vivo. An accurate measurement of antibody activity may be of value in the evaluation of TTP's clinical course and to help predict the imminent relapse of TTP. By using this method, we can determine the ADAMTS13 autoantibody inhibitory titers using a similar approach as described for the determination of Bethesda unit (BU) in patients with a factor VIII inhibitor. As shown in table 2, ADAMTS13 activity was determined after pooled normal plasma (PNP) was mixed with an equal volume of patient plasma made at various dilutions. Afterwards, the ADAMTS13 activity from each sample was divided by the ADAMTS13 activity obtained from PNP control to obtain the residual activity. The BU was then extrapolated from the residual activity according to the standard Bethesda graph. Next, the BU from each diluted sample was calculated by multiplying sample's dilution factors. Finally, ADAMTS13 antibody inhibitory titer (BU) in this patient was determined by averaging BU values obtained from three diluted samples that gave rise to a residual activity around 50%.

TABLE I

Clinical Characteristics
Table 1: Characterisitcs of Patients with a Diagnosis of Idiopathic TTP

| | | | | Initial Presentation | | | | | |
|---|---|---|---|---|---|---|---|---|---|
| Patient # | Sex | Age | Race | Initial ADAMTS-13 by SELDI | Mixing studies, Residual ADAMTS-13 activity | Number of occurences over duration of follow-up (months) | Platelet count (150-400) | LDH (100-190) | Haptoglobin (20-230) |
| 1 | F | 53 | AA | <2.5% | 85.3% | 2/11 | 8 | 1415 | <8 |
| 2 | M | 47 | White | <2.5% | 23.5% | 2/25 | 11 | 1109 | <8 |
| 3 | F | 48 | AA | 4.1% | 8.5% | 2/23 | 7 | 1129 | <8 |
| 4 | F | 22 | AA | 14.6% | 23.3% | 4/15 | 7 | 1289 | <8 |
| 5 | M | 47 | AA | <2.5% | 11.8% | 2/21 | 22 | 549 | <8 |
| 6 | F | 50 | White | <2.5% | 9.0% | 3/37 | 6 | 2054 | <8 |
| 7 | M | 31 | White | <2.5% | 10.4% | 2/21 | 9 | 2618 | <8 |
| 8 | F | 20 | White | <2.5% | 18.2% | 3/17 | 8 | 700 | <8 |
| 9 | F | 40 | AA | <2.5% | 22.4% | 2/17 | 6 | 1302 | <8 |
| 10 | F | 48 | White | <2.5% | 8.6% | 2/13 | 8 | 647 | <8 |
| 11 | F | 25 | White | <2.5% | 15.3% | 2/15 | 11 | 1112 | <8 |
| 12 | F | 37 | White | <2.5% | 8.6% | 3/16 | 9 | 2338 | <8 |
| 13 | M | 48 | White | <2.5% | 84.6% | 2/13 | 5 | 2445 | <8 |
| 14 | F | 39 | White | <2.5% | 9.3% | 3/40 | 3 | 1227 | <8 |
| 15 | M | 30 | White | <2.5% | 54.1% | 2/13 | 5 | 1544 | <8 |
| *16 | M | 51 | AA | <2.5% | 8.4% | 2/11 yrs | 7 | 724 | <8 |

| | | Initial Presentation | | | |
|---|---|---|---|---|---|
| Patient # | Hg (13.2-17.3) | Bilirubin, indirect (0-0.9) | Schistocytes | Renal failure | Changes of Mental status |
| 1 | 6.3 | 2 | X | No | |
| 2 | 8.1 | 3.8 | X | X | |
| 3 | 9.4 | 2.5 | X | No | |
| 4 | 8.1 | 2.5 | X | No | |
| 5 | 10.5 | 1.1 | X | No | |
| 6 | 7.6 | 1.7 | X | No | |
| 7 | 5.4 | 6.6 | X | X | X |
| 8 | 6.1 | 1.6 | X | No | |
| 9 | 6.2 | 4.1 | X | X | X |
| 10 | 8.1 | 2 | X | no | |
| 11 | 6.2 | 2.5 | X | No | |
| 12 | 5.9 | 3.4 | X | No | |
| 13 | 7.2 | 2.8 | X | X | X |
| 14 | 8.2 | 2.5 | X | No | |
| 15 | 6.7 | 1.4 | X | X | |
| *16 | 9.2 | 3.4 | X | X | |

*First occurrence is recorded from patient medical history. Laboratory results in the table were from second occurrence

TABLE 2

Determination of ADAMTS13 autoantibody titer in Bethesda unit (BU)

| Sample dilution in saline | Sample mix (equal volume) | ADAMTS13 activity | Residual ADAMTS 13 activity | BU calculated from the residual activity | Final BU after multiplying by the dilution factor |
|---|---|---|---|---|---|
| Control | PNP + saline | 50.0% | | | |
| Undiluted | PNP + undiluted patient plasma | 1.4% | 2.8% | 3.1 | 3.1 |
| 1:2 | PNP + patient plasma at 1:2 dilution | 1.7% | 3.4% | 3.1 | 6.1 |
| 1:4 | PNP + patient plasma at 1:4 dilution | 9.5% | 19.0% | 2.4 | 9.4 |
| 1:8 | PNP + patient plasma at 1:8 dilution | 16.8% | 33.5% | 1.4 | 11.2 |
| 1:16 | PNP + patient plasma at 1:16 dilution | 27.8% | 55.7% | 0.8 | 12.5 |
| 1:32 | PNP + patient plasma at 1:32 dilution | 37.8% | 75.5% | 0.4 | 12.8 |
| | | | | | Average = 12.16 |

Various modifications and variations of the described products and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A process for detecting an enzyme activity, comprising:
preparing a sample by contacting a blood product with a substrate comprising a cleavage site of the enzyme and a tag moiety, wherein cleavage of the substrate by the enzyme produces a cleavage product having the tag moiety; and then
contacting the sample with a surface moiety that is disposed on a Surface Enhanced Laser Desorption/Ionization (SELDI) sample chip and that binds the tag moiety of the cleavage product, such that binding of the surface moiety to the cleavage product indicates activity of the enzyme in the blood product.

2. The process of claim 1, further comprising, after contacting the sample with the surface moiety, subjecting the SELDI sample chip to SELDI mass spectrometry to identify the cleavage product.

3. The process of claim 2, further comprising, after contacting the sample with the surface moiety and prior to subjecting the SELDI sample chip to SELDI mass spectometry,
washing the SELDI sample chip to remove blood product components that do not selectively bind to the surface moiety on the SELDI sample chip.

4. A process for detecting ADAMTS-13 activity, comprising:
preparing a sample by contacting a blood product with a substrate comprising an ADAMTS-13 cleavage site and a tag moiety, wherein cleavage of the substrate by ADAMTS-13 produces a cleavage product having a the tag moiety; and then
contacting sample with a surface moiety that is disposed on a SELDI sample chip and binds the tag moiety of the cleavage product, such that binding of the surface moiety to the cleavage product indicates ADAMTS-13 activity in the blood component.

5. The process of claim 4, further comprising, after contacting the sample with the surface moiety,
washing the SELDI sample chip to remove blood product components that do not selectively bind to the surface moieties of the SELDI sample chip; and then
subjecting the SELDI sample chip to SELDI mass spectrometry to identify the cleavage product.

6. The process of claim 5, further comprising quantifying the amount of cleavage product present in the sample.

7. The process of claim 4, further comprising, prior to contacting the sample with the surface moiety,
terminating the cleavage and adding to the sample an internal control that binds the surface moiety.

8. The process of claim 7, further comprising,
washing the SELDI sample chip after the internal control is added to the sample; and then
subjecting the SELDI sample chip to SELDI mass spectrometry to identify and determine the amount of the cleavage product and the internal control.

9. The process of claim 4, wherein the tag moiety is a selected from the group consisting off a maltose binding protein tag, a glutathione-S-transferase (GST) tag, a biotin tag, an avidin tag and a histidine tag.

10. The process of claim 4, wherein the tag moiety comprises a histidine tag.

11. The process of claim 4, wherein the SELDI sample chip is charged with a compound comprising a metal selected from the group consisting of nickel, iron II, iron III, calcium, magnesium, manganese, copper, zinc and mixtures thereof.

12. The process of claim 4, wherein the SELDI sample chip is an IMAC (immobilized metal affinity capture) ProteinChip.

13. The process of claim 4, wherein the SELDI sample chip is charged with nickel sulfate.

14. The process of claim 4, wherein the contacting of the blood product with the substrate is for a period which ranges from about 1 to about 20 hours.

15. A process for detecting ADAMTS-13 activity comprising:
preparing a sample by contacting a blood product with a substrate comprising an ADAMTS-13 cleavage site and a tag moiety, wherein cleavage of the substrate by ADAMTS-13 produces a cleavage product having the tag moiety; and
contacting the sample with a surface moiety that is disposed on a SELDI sample chip and binds the tag moiety of the cleavage product;
removing from the SELDI sample chip blood product components that do not selectively bind to the surface moieties moiety on the SELDI sample chip; and then subjecting the SELDI sample chip to a SELDI mass spectrometer to identify the cleavage product, which indicates ADAMTS-13 activity.

16. The process of claim 15, further comprising, prior to contacting the sample with the surface moiety,
terminating the cleavage and adding to the sample an internal control that binds the surface moiety.

17. The process of claim 15, further comprising quantifying the amount of cleavage product present in the sample.

18. The process of claim 15, wherein the amount of cleavage product present in the reaction sample is quantitatively compared to at least one internal control.

19. The process of claim 18, wherein the amount of cleavage product is determined by the ratio of the amount of cleavage product measured by the mass spectrometer to the amount of the internal control measured by the mass spectrometer.

20. The process of claim 15, wherein the tag moiety is a selected from the group consisting of a maltose binding protein tag, a glutathione-S-transferase (GST) tag, a biotin tag, an avidin tag and a histidine tag.

21. The process of claim 15, wherein the SELDI sample chip is charged with a compound comprising a metal selected from the group consisting of nickel, iron II, iron III, calcium, magnesium, manganese, copper, zinc and mixtures thereof.

22. The process of claim 15, wherein the tag moiety is a histidine tag and the SELDI sample chip is charged with a compound comprising nickel.

23. The process of claim 22, wherein the SELDI sample chip is an IMAC (immobilized metal affinity capture) ProteinChip charged with nickel sulfate.

24. The process of claim 15, wherein the contacting of the blood product with the substrate is for a period which ranges from about 1 to about 20 hours.

25. The process of claim 24, wherein the period ranges from about 1 hours to about 2 hours to determine a level of ADAMTS-13 activity as low as 2.5%.

26. The process of claim 24, wherein the incubation period ranges from about 10 hours to about 40 hours to determine a level of ADAMTS-13 activity as low as 0.31%.

27. The process of claim 15, wherein the substrate is purified.

28. The process of claim 15, wherein the substrate is engineered.

29. The process of claim 15, wherein the substrate comprises a recombinant protein with a tag moiety that produces a cleavage product upon proteolysis.

30. The process of claim 15, wherein the SELDI mass spectrometer is a SELDI-TOS mass spectrometer.

31. The process of claim 15, wherein the process detects the ability of an ADAMTS-13 antibody inhibitor from a patient to neutralize ADAMTS-13 activity in normal plasma.

32. The process of claim 15, wherein the amount of the cleavage product is used to diagnose thrombotic thrombocytopenic purpura (TTP).

33. The process of claim 15, wherein the amount of the cleavage product is used to diagnose blood clotting disorders.

34. The process of claim 33, wherein the blood clotting disorder is selected from the group consisting of heart attack, stroke, deep vein thrombosis and arterial thrombodic disorders.

35. The process of claim 15, wherein the amount of the cleavage product is used to assess a response to therapy.

36. The process of claim 15, wherein the amount of the cleavage product is used to predict recurrence of TTP.

* * * * *